US00PP26020P3

(12) United States Plant Patent

Koppman et al.

(10) Patent No.: US PP26,020 P3

(45) Date of Patent: Oct. 27, 2015

(54) *AGONIS FLEXUOSA* PLANT NAMED 'AFTER SHOCK'

(50) Latin Name: *Agonis flexuosa*
Varietal Denomination: After Shock

(71) Applicants: James F. Koppman, Huskisson (AU); Jacqueline A. Koppman, Falls Creek (AU); Greg Lowe, Tumbi Umbi (AU)

(72) Inventors: James F. Koppman, Huskisson (AU); Jacqueline A. Koppman, Falls Creek (AU); Greg Lowe, Tumbi Umbi (AU)

( * ) Notice: Subject to any disclaimer, the term of this patent is extended or adjusted under 35 U.S.C. 154(b) by 65 days.

(21) Appl. No.: 13/999,607

(22) Filed: Mar. 12, 2014

(65) Prior Publication Data

US 2015/0264850 P1 Sep. 17, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para

(74) *Attorney, Agent, or Firm* — Samuel R. McCoy, Jr.

(57) ABSTRACT

'After Shock' is a distinctive variety of *Agonis flexuosa* which is characterized by the combination of strong basal branching, short stem internodes, deep red foliage, and both shorter and narrower leaves. As a shrub form of *Agonis flexuosa*, 'After Shock' has a short, upright to slightly weeping growth habit with an overall plant height of approximately 8 ft (unpruned), a width of approximately 5 ft (unpruned).

4 Drawing Sheets

Latin name of the genus and species: The Latin name of the genus and species of the novel variety disclosed herein is *Agonis flexuosa.*

Variety denomination: The inventive variety of *Agonis flexuosa* disclosed herein has been given the variety denomination 'After Shock'.

BACKGROUND OF THE INVENTION

The present invention relates to a new and distinct perennial variety of *Agonis flexuosa*, which has been given the variety denomination of 'After Shock'. Its market class is that of an ornamental shrub or small tree. 'After Shock' is intended for use in landscaping as a small specimen tree or hedge shrub in mild Mediterranean climates.

An application for plant breeders' rights for 'After Shock' has been lodged with the Australian Plant Breeders Rights Office and was accepted on Mar. 14, 2012 (under Application No. 2010/319).

Parentage: The *Agonis flexuosa* variety 'After Shock' was selected as a whole plant mutation from *Agonis flexuosa* 'Jervis Bay After Dark' (unpatented, Australian Plant Breeders Rights application no. 1997/225) in 2007 at a commercial plant tissue culture laboratory and propagation facility in Tumbi Umbi in the state of New South Wales, Australia, among vegetative propagules of 'Jervis Bay After Dark'. The instant plant was identified as possessing the same dark red stem and foliage color as the parent but further exhibited several improved characteristics such as a more compact and dense growth habit due to strong basal branching habit, shortened stem internode length, and smaller leaves. The instant plant was isolated and given the name 'After Shock'.

Asexual Reproduction: The new variety 'After Shock' was first asexually propagated by vegetative cuttings in 2007 and has been asexually propagated since that time by division and micropropagation in order to advance nursery and landscape trials for distinctness, uniformity and stability of the distinct characteristics. Said characteristics of the inventive 'After Shock' variety have proven to be stable through 10 successive generations produced by both cuttings as well as micropropagation.

SUMMARY OF THE INVENTION

'AFTER DARK' is a distinctive variety of *Agonis flexuosa* which is characterized by the combination of strong basal branching, short stem internodes, deep red foliage, and both shorter and narrower leaves. As a shrub form of *Agonis flexuosa*, 'After Shock' has a short, upright to slightly weeping growth habit with an overall plant height of approximately 2.5 m (unpruned), a width of approximately 1.5 m (unpruned).

BOTANICAL DESCRIPTION OF THE PLANT

Figure 1:
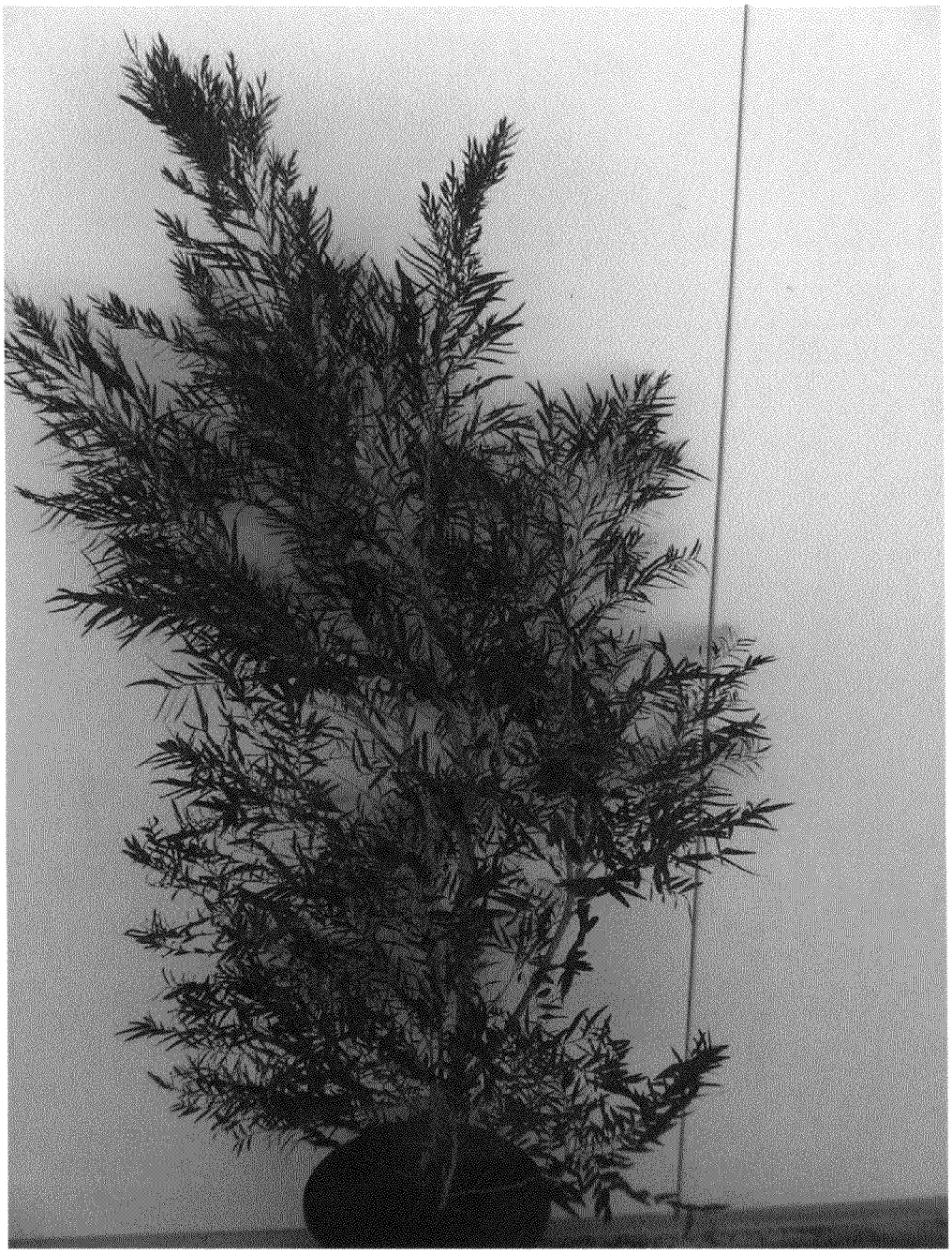
FIG. 1 shows an exemplary 'After Shock' plant, unpruned, at approximately 24-months old.

The following is a detailed botanical description of a new and distinct variety of *Agonis flexuosa* known as 'After Shock' based upon observations of 18-month old plants grown from rooted cuttings into 5 gallon in a greenhouse near Watsonville CA from autumn of 2010 to spring of 2012. Plants were grown and maintained in accordance with standard greenhouse production protocol. No pest control measures were taken. Plant observations and descriptions were taken in early spring of 2012.

Those skilled in the art will appreciate that certain characteristics will vary with older or, conversely, with younger plants. 'After Shock' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 edition.

In mild climates, corresponding approximately to USDA Hardiness Zones 9b through 11, 'After Shock' is an evergreen shrub with an upright to slightly weeping habit and dark red foliage similar to the parent, with small leaves and short internodes which creates a dense growth habit. These and other features of the instant variety will become apparent to one of ordinary skill in the art from the botanical description below.

A botanical description of 'After Shock' and comparisons with other varieties of *Agonis flexuosa* are provided below.

Technical Description of the Variety.

Propagation: Micropropagation or vegetative cutting propagation using semi-green wood cuttings, rooted into soilless propagation media, with or without the aid of rooting hormones. Time to fully root cuttings in propagation trays is approximately 12 to 16 weeks, depending on production inputs, site location and geographic location.

Plant characteristics: Growth habit upright to slightly weeping with strong basal branching and strong shoot density; recorded height of the oldest mature plants is approximately 2.5 meters and width is approximately 1.5 meters but it is believed that, with time and under optimal conditions, the instant plant could reach a height of 4.5-5.0 meters tall and a width of approximately 3.0 meters wide.

Stems: Strong branching habit, branch angles acute, young stems have a flexuous (or "zig zag"-like) habit. Shape of the stem is generally round with a smooth and corky to semi-hard texture, hardening as branches mature. Immature stems are greyed-red in color (approximately RHS 181A) while mature woody stems approximate to greyed-orange (165B). Stem internode length is short at approximately 15 mm for new shoots, 20-25 mm for secondary stems and 30-35 mm for the main stem.

Leaves: The simple leaves are petiolate (petiole is very small and almost indistinguishable) and the arrangement is alternate and distichous. Shape is lanceolate, margins are ciliate, apex acute, base cuneate. Leaf venation consists of a prominent midrib with pinnate tertiary veins originating from said midrib and, additionally, prominent secondary vein originating from the petiole and running longitudinally along the leaf margin; one such secondary vein per side of the leaf. Immature foliage color ranges from greyed-purple (185A) to greyed-purple (187A) on both the adaxial and abaxial surfaces whereas the mature foliage ranges in color from yellow green (146C) to yellow-green (147C) to greyed-purple (187A) on both the adaxial and abaxial, with the prominent and general color being greyed-purple (187A). Leaf texture in all stages is smooth and finely pubescence on both the adaxial and abaxial surfaces. Length of mature leaves is approximately 60 mm and width is approximately 12 mm.

Inflorescence, flowers and fruiting: Not yet observed.

Cold and heat tolerance: 'After Shock' has not been observed under all conditions but it is believed to possess cold and heat tolerance typical of *Agonis flexuosa.*

Drought tolerance: 'After Shock' has good drought tolerance typical of *Agonis flexuosa* once established.

Pest resistance: No known insect pests. 'AFTER DARK' has disease tolerance typical of *Agonis flexuosa.*

Environmental tolerances: Similar to the species; tolerates low fertility and a wide range of soil conditions although intolerant of poor drainage.

Comparisons with other *Agonis*

The most similar varieties of common knowledge are the parent plant, *Agonis flexuosa* 'Jervis Bay After Dark' and another progeny of the parent, *Agonis flexuosa* 'Jedda's Dream'. While there are certain similarities between the instant plant and the two comparators, namely foliage color, stem color and lineage, there are several characteristics present in 'After Shock' that distinguish 'After Shock' from comparators.

Figure 2:
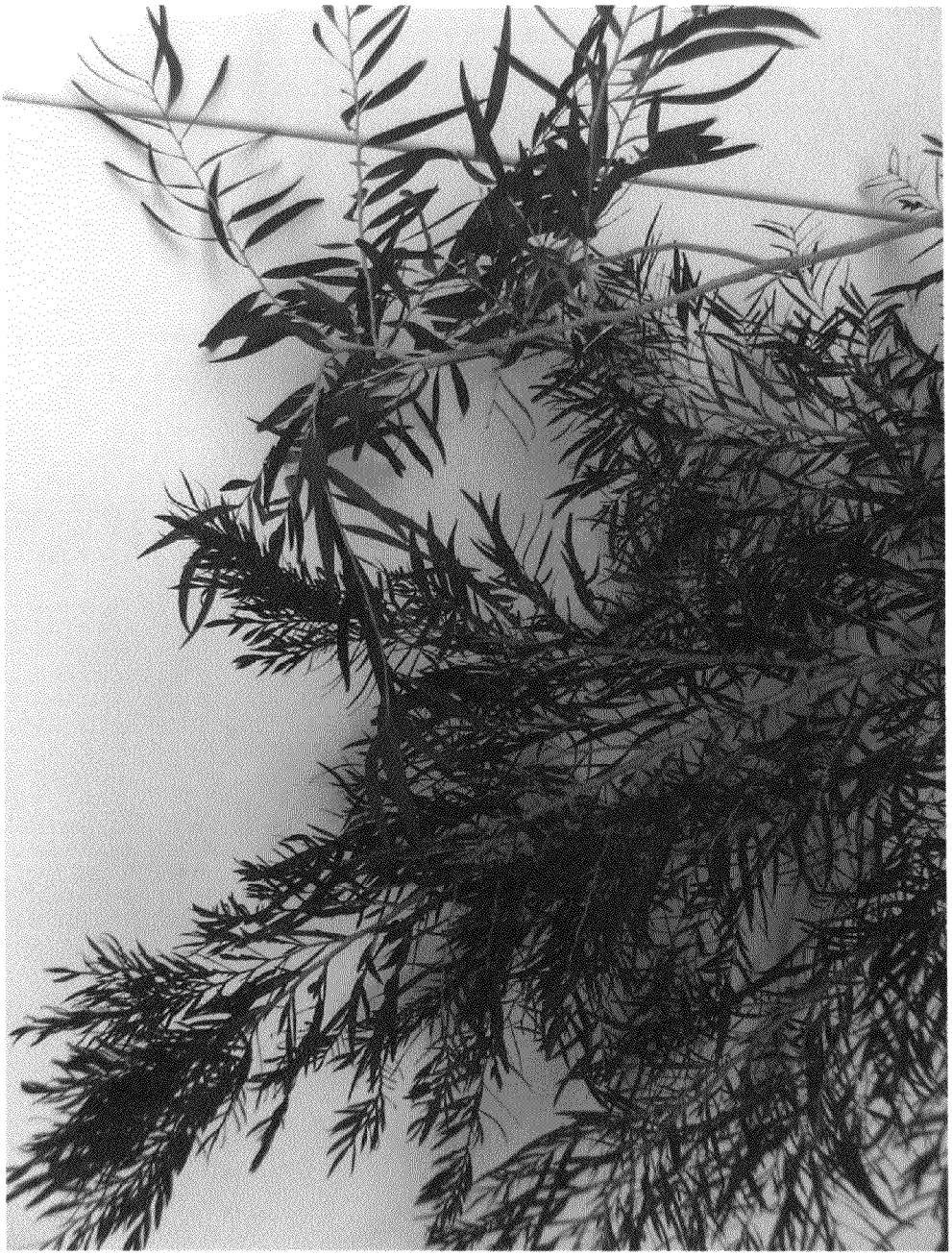
FIG. 2 shows a comparison of habit (i.e. leaf size, branching, and internode length) with the bushier 'After Shock' on the left and the parent 'Jervis Bay After Dark' on the right.
Figure 3:
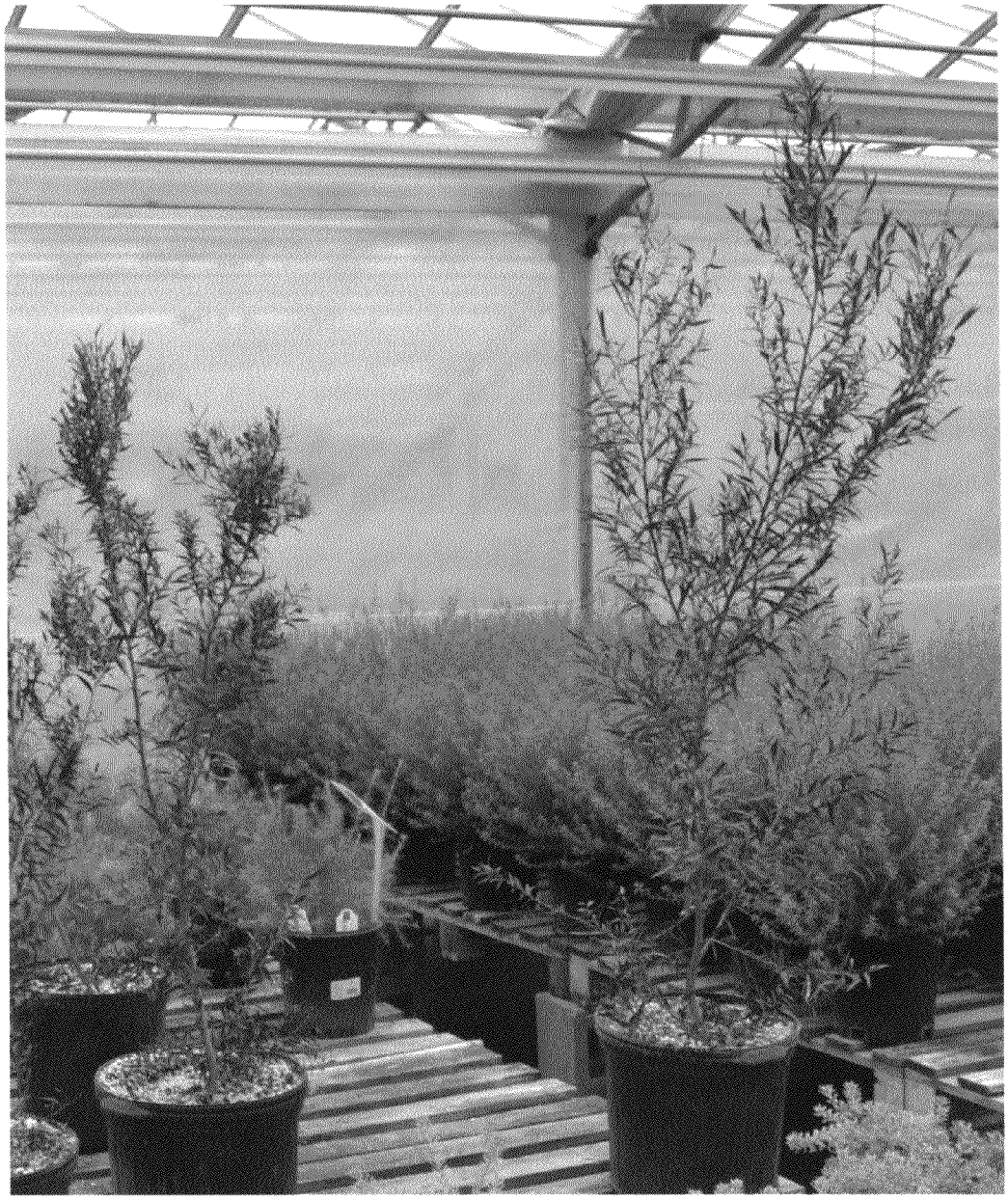
FIG. 3 shows a comparison of general habit and size of 'After Shock' (left) versus the parent 'Jervis Bay After Dark' (right). Plants are approximately 14 months old (not yet mature).

While 'After Shock' and 'Jervis Bay After Dark' both have an upright to slightly weeping growth habit, 'After Shock' has a shorter plant height, with 18 month-old 'After Shock' plants measuring 120-140 cm (unpruned), compared to 'Jervis Bay After Dark' plants which had a measured height of approximately 150-170 cm (unpruned); see FIG. 3 for reference. 'After Shock' has strong basal branching and retains this density at maturity whereas 'Jervis Bay After Dark' has weaker basal branching with a more open habit once mature. 'After Shock' has a smaller leaf compared to its parent; see FIG. 2 for reference. The leaf dimensions of 'After Shock' are approximately 60 mm long and 12 mm wide whereas *Agonis flexuosa* 'Jervis Bay After Dark' has larger leaves with dimensions of approximately 80 mm long and 12 mm wide. Also, 'After Shock' has shorter stem internodes. Internode lengths of 'After Shock' are approximately 15 mm for new shoots, 20-25 mm for secondary stems and 30-35 mm for the main stem whereas internode lengths for 'Jervis Bay After Dark' are approximately 20 mm for new shoots, 30 mm for secondary stems and 40-45 mm for the main stem.

Figure 4:
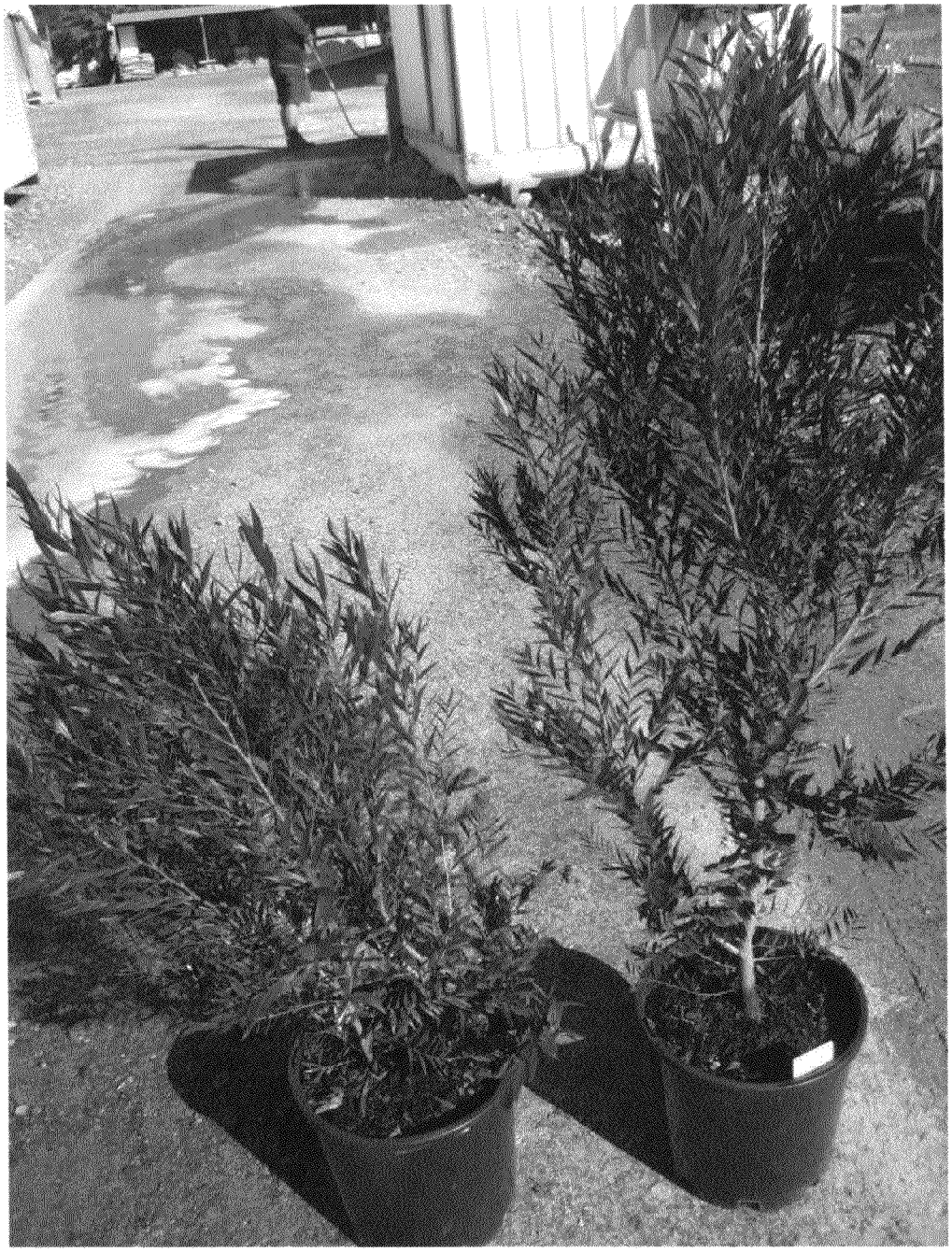
FIG. 4 shows a comparison of general habit and size of 'After Shock' (right) versus comparator 'Jedda's Dream' (left). Plants are approximately 24 months old and mature.

'After Shock' is also similar to 'Jedda's Dream', another progeny of the parent variety of the instant plant. Both retain the dark red stem and foliage color from the parent, both have a shorter plant height than the parent, both have smaller leaves than the parent and both are more compact than the parent. However, there are certain distinguishable characteristics between these two comparators. 'After Shock' has an upright to slightly weeping growth habit while 'Jedda's Dream' has a compact and bushy habit; see FIG. 4 for reference. By comparison, 'After Shock' has a taller plant height, with 24 month-old 'After Shock' plants measuring 120-140 cm (unpruned), compared to 'Jedda's Dream' plants which had a measured height of approximately 70-90 cm (unpruned). Both have strong basal branching and leaves that are approximately the same size. However, 'After Shock' has longer stem internode lengths when compared to 'Jedda's Dream'. Internode lengths of 'After Shock' are approximately 15 mm for new shoots, 20-25 mm for secondary stems and 30-35 mm for the main stem whereas internode lengths for 'Jedda's Dream' are approximately 10-12 mm for new shoots, 10-22 mm for secondary stems and 20-25 mm for the main stem. 'After Shock' also exhibits stronger plant vigor by comparison to 'Jedda's Dream' which translates to a faster rate of growth, less mortality during propagation and production and a higher survival rate once transplanted into the landscape.

That which is claimed is:

1. A new and distinct variety of *Agonis flexuosa* plant named 'After Shock', substantially as described and illustrated herein.

* * * * *